(12) United States Patent
Burke et al.

(10) Patent No.: US 6,511,815 B1
(45) Date of Patent: Jan. 28, 2003

(54) METHOD FOR QUANTITATING COMPETITIVE BINDING OF MOLECULES TO PROTEINS UTILIZING FLUORESCENCE POLARIZATION

(75) Inventors: Thomas J. Burke, Madison, WI (US); Randall E. Bolger, Oregon, WI (US); Kerry M. Ervin, Middleton, WI (US); Robert G. Lowery, Brooklyn, WI (US); William J. Checovich, Madison, WI (US)

(73) Assignee: PanVera LLC, Madison, WI (US)

( * ) Notice: Subject to any disclaimer, the term of this patent is extended or adjusted under 35 U.S.C. 154(b) by 0 days.

(21) Appl. No.: 09/467,628

(22) Filed: Dec. 20, 1999

Related U.S. Application Data (62) Division of application No. 08/904,371, filed on Aug. 1, 1997, now abandoned.
(60) Provisional application No. 60/023,034, filed on Aug. 2, 1996.

(51) Int. Cl.[7] .......................... G01N 33/53; C12Q 1/68; C12N 15/12; C12N 5/00; C07K 14/00
(52) U.S. Cl. .......................... 435/7.8; 435/6; 435/69.1; 435/325; 435/320.1; 530/350
(58) Field of Search .......................... 435/6, 7.8, 69.1, 435/325, 320.1; 530/350

(56) References Cited

U.S. PATENT DOCUMENTS 5,445,935 A * 8/1995 Royer .......................... 435/6

OTHER PUBLICATIONS

Hwang et al. Donor–acceptor tetrahydrochrysenes, Inherently fluorescent, high–affinity ligands for the estrogen receptor: binding and fluorescence characteristics and fluorometric assay of receptor. *Biochemistry.* 1992. vol. 31 pp. 11536–11545.*

Aucouturier, P. et al. Fluorescence Polarization Immunoassay of Estradiol. *Diag Immunol*, 1983. vol 1. pp. 310–314.

Checovich, W. J. et al. Fluorescence Polarization—A New Tool for Cell and Molecular Biology. *Nature.* May 18, 1995. vol. 375, pp. 254–256.

Miksicek, R. J. et al. Studies Using Fluorescent Tetrahydrochrysene Estrogens for In Situ Visualization of the Estrogen Receptor in Living Cells. *Molecular Endocrinology.* 1995, vol. 9, pp. 592–604.

* cited by examiner

*Primary Examiner*—David S. Romeo
*Assistant Examiner*—Joseph F. Murphy
(74) *Attorney, Agent, or Firm*—Vertex Pharmaceuticals, Incorporated; Andrew S. Marks (57) ABSTRACT

The system comprises mixing a fluorescence-emitting compound that binds to the steroid hormone receptors in a solution containing the steroid hormone receptors. Then, measuring the fluorescence polarization of the solution. Subsequently, incubating the solution with at least one molecule that may compete with the compound for interaction with the steroid hormone receptors. Measuring the fluorescence polarization of the solution again. Finally, comparing the fluorescence polarization measurements to quantify any competitive interaction.

9 Claims, 10 Drawing Sheets

|  | 535 nm | 485 nm |
| --- | --- | --- |
| Equation 1 | | |
| Variables | | |
|   BOTTOM | 60.23 | 69.32 |
|   TOP | 418.4 | 391.5 |
|   LOGEC50 | 0.2260 | 0.3756 |
|   HILLSLOPE | 1.322 | 1.223 |
|   EC50 | 1.683 | 2.374 |
| Std. Error | | |
|   BOTTOM | 2.930 | 3.253 |
|   TOP | 3.395 | 4.337 |
|   LOGEC50 | 0.01744 | 0.02364 |
|   HILLSLOPE | 0.06271 | 0.07328 |
| 95% Confidence Intervals | | |
|   BOTTOM | 53.85 to 66.62 | 62.23 to 76.40 |
|   TOP | 411.0 to 425.8 | 382.1 to 401.0 |
|   LOGEC50 | 0.1880 to 0.2640 | 0.3240 to 0.4271 |
|   HILLSLOPE | 1.186 to 1.459 | 1.064 to 1.383 |
|   EC50 | 1.542 to 1.836 | 2.109 to 2.673 |
| Residuals | | |
|   Points above curve | 9 | 7 |
|   Points below curve | 7 | 9 |
|   Number of runs | 10 | 8 |
|   P value (runs test) | 0.8059 | 0.4266 |
|   Deviation from Model | Not Significant | Not Significant |

| THC ESTER CONCENTRATION (nM) | DMSO CONCENTRATION (%) | POLARIZATION (mP) |
|---|---|---|
| 20 | 25 | 232 |
| 20 | 12.5 | 251 |
| 20 | 6.25 | 226 |
| 20 | 3.13 | 164 |
| 20 | 1.56 | 148 |
| 20 | 0.78 | 99 |
| 20 | 0.39 | 81 |
| 20 | 0.20 | 52.9 |
| 20 | 0.10 | 62.5 |
| 20 | 0.05 | 40.7 |
| 20 | 0 | 48 |

| THC KETONE CONCENTRATION (nM) | DMSO CONCENTRATION (%) | POLARIZATION (mP) |
|---|---|---|
| 15 | 5 | 206 |
| 15 | 0 | 137 |

| THC AMIDE CONCENTRATION (nM) | DMSO CONCENTRATION (%) | POLARIZATION (mP) |
|---|---|---|
| 25 | 5 | 127 |
| 12.5 | 5 | 49.9 |
| 6.25 | 5 | 55.8 |
| 3.13 | 5 | 55 |

Fig. 8

| | |
|---|---|
| glycerol, 20% | isoamyl alcohol, 20% |
| ethylene glycol, 20% | butanol, 20% |
| ethoxyether, 20% | acetonitrile, 20% |
| ethanolamine, 20% | KCl, 2 M |
| Polyethylenimine, 6.25% | triethylamine, 20% |
| urea, 200 mM | formaldehyde, 20% |
| formaldehyde, 10 mM | Tris-HCl, 1M, pH 8 |
| imadazol, 1 M | Imadazole, 100 mM, pH 7 |
| acetone, 20% | MOPS buffer, 50 mM, pH 6.8 |
| methanol, 20% | $KPO_4$, 1M, pH 6.5 |
| sulfonyl diethanol, 20% | glycine, 25 mM, pH 9.6 |
| MOPS buffer, 0.5 M, pH 6.8 | HEPES, 1M, pH 8 |
| HEPES buffer, 1 M | boric acid, 100 mM, pH 9.5 |
| $MgCl_2$, 20 mM | Dimethylformamide, 20% |
| $NiCl_2$, 100 mM | 2-mercaptoethanol, 13.2 M |
| glycine, 100 mM, pH2 | Polyvinylpyrollidone, 10% |
| NaCl, 5 M | Ficoll, 10% |
| SDS detergent, 0.02% | Sorbitol, 10% |
| heptaldehyde, 20% | NP40 Detergent, 0.1% |
| SB12 detergent | octylglucopyroanoside detergent |
| polyethyleneglycol | sarcosyl detergent |
| Triton-X 100 detergent | Triton-X 114 detergent |
| sodium deoxycholate | guanidine hydrochloride |
| urea | CHAPS detergent |
| Brij 35 detergent | Tween 20 detergent |
| dithiothreitol, 1M | Bovine gamma globulin |

Fig. 9

| | |
|---|---|
| Average Starting Polarization (mP) of Fluormone ES1 | 79 |
| Average Starting Polarization (mP) of Fluormone after Addition of 2% DMSO | 253 |

| Compound Added to Correct DMSO Effect on Fluormone ES1 | Polarization (mP) after addition of Compound |
|---|---|
| N,N dimethylformamide | 79 |
| 2- mercaptoethanol | 120 |
| acetonitrile | 129 |
| acetone | 131 |
| triethylamine | 153 |
| formamide | 159 |
| 2 M KCl | 159 |
| ethylene glycol | 161 |
| butanol | 162 |
| 0.2 M urea | 181 |
| 1% sodium dodecyl sulfate | 216 |
| 10 M formaldehyde | 235 |
| 100 mM nickel chloride | 238 |
| 1 M dithiothreitol | 261 |
| 100 mM glycine, pH 2.0 | 276 |
| 1 M magnesium chloride | 287 |
| 1 M sodium phosphate | 340 |

Fig. 10

METHOD FOR QUANTITATING COMPETITIVE BINDING OF MOLECULES TO PROTEINS UTILIZING FLUORESCENCE POLARIZATION

CROSS-REFERENCE TO RELATED APPLICATIONS

This application is a divisional of U.S. patent application Ser. No. 08/904,371 filed Aug. 1, 1997, now abandoned, which claims priority to U.S. provisional patent application Serial No. 60/023,034, filed Aug. 2, 1996, now expired.

FEDERALLY SPONSORED RESEARCH

N.A.

FIELD

The field of the invention relates to the detection of molecules which bind to steroid hormone receptors by measuring the fluorescence polarization emission from a molecule. In particular, fluorescence-emitting compounds are used in competitive assays to measure binding of molecules to steroid hormone receptors such as estrogen receptor.

BACKGROUND OF THE INVENTION

The use of labeled oligonucleotides as probes in molecular analysis has been an important technique in molecular biology. Oligonucleotides have been labeled with radioisotopes, enzymes or fluorescent molecules. Because of the relatively low molecular weights of oligonucleotides, and the common availability of instrumentation for their automated synthesis, oligonucleotides are often used in blot-hybridization procedures or in gel-retardation assays for the detection and qualitative evaluation of macromolecules with which they may associate. These macromolecules may be either proteins, RNA molecules or DNA molecules.

In a standard blot-hybridization procedure, the target macromolecule is separated by electrophoresis in a gel matrix, commonly agarose or polyacrylamide. It is then transferred to a membrane in such a way as to preserve its relative spatial positioning within the gel matrix and fix it stably to the membrane. Alternatively, the macromolecule may be attached to the membrane without prior electrophoresis. The presence of the macromolecule on the membrane is determined by binding to it a labeled oligonucleotide and subjecting the complex to autoradiography or, if the oligonucleotide is labeled with radioisotope, by scintillation counting.

In a standard gel retardation assay an oligonucleotide that has been labeled with radioisotope or other detectable moiety is electrophoresed in a gel matrix, commonly made of agarose or acrylamide, under non-denaturing conditions. The labeled oligonucleotide is also associated with a protein that may bind to the oligonucleotide and the mixture is electrophoresed on a gel, commonly in a neighboring lane, for comparing with the unassociated oligonucleotide. Because of its higher molecular weight and lower net negative charge, the protein will exhibit lower mobility in the gel than the unassociated oligonucleotide. If the oligonucleotide forms a stable complex with the protein, it will also exhibit a lower mobility than that of the unassociated oligonucleotide. Comparison of the mobility of the oligonucleotide mobility in the presence and absence of the protein allows qualitative determination of whether a complex forms between the two macromolecules. These basic methods are used for a very large variety of determinations in basic genetic research, genetic engineering, the medical sciences, and agricultural testing.

Additionally, fluorescence-labeled compounds other than oligonucleotides are used in assays to measure binding of molecules to biological substances. For example, the observation and measurement of hormone binding to hormone receptors is a technique currently in demand. Typically, a steroid hormone such as estradiol binding to a hormone receptor such as estrogen receptor is performed using radioactive hormone and receptor protein. The labeled hormone is added in excess to the receptor in a buffer and allowed to reach equilibrium. The bound hormone is then separated from the free hormone and quantitated. The binding affinity between the hormone and the receptor can be mathematically determined.

Furthermore, an assay has been described in a publication that does not require a separation step. It is based on a modified fluorescent hormone (Hwang et. al. Biochemistry 31:11536–45, 1992). The assay uses the observation that when the hormone and receptor bind, the fluorescence intensity of the hormone decreases proportional to binding. Free hormone has a high fluorescence intensity and the bound hormone has a low fluorescence intensity. However, several components of the binding mixture can affect the intensity other than the receptor. The polarity of the solvent and non-specific binding molecules can have significant affects on the intensity, which can be incorrectly interpreted as hormone/receptor binding.

Another detection method described in the early 1900's utilizes fluorescence polarization. Fluorescence polarization assay techniques are based on the principle that a fluorescently labeled compound will emit fluorescence when excited by plane polarized light, having a degree of polarization inversely related to its rate of rotation. If the labeled molecule remains stationary throughout the excited state it will emit light in the same polarized plane; if it rotates while excited, the light emitted is in a different plane.

For example, when a large labeled molecule is excited by plane polarized light, the emitted light remains highly polarized because the fluorophore is constrained (by its size) from rotating between light absorption and fluorescent light emission. When a smaller molecule is excited by plane polarized light, its rotation is much faster than the large molecule and the emitted light is more depolarized. The emitted light has a degree of polarization that is inversely proportional to the molecular rotation. Therefore, small molecules have low polarization values and large molecules have high polarization values.

Fluorescence polarization assays are homogeneous in that they do not require a separation step such as centrifugation, filtration, chromatography, precipitation or electrophoresis. Assays can be performed in real time, directly in solution and do not require an immobilized phase. For example, fluorescence polarization has been used to measure enzymatic cleavage of large fluorescein labeled polymers by proteases, DNases and RNases.

SUMMARY

The present invention is an easy method for detecting and quantitating a complex between molecules, such as hormones and nucleic acids interacting with steroid hormone receptors. The invention utilizes the measurement of fluorescence polarization of an intrinsic fluorescence-emitting compound such as a fluorescence-emitting hormone as well as emission from a fluorophore covalently coupled to an oligonucleotide. The fluorescence-emitting compound and the fluorescent oligonucleotide produce a low polarization quantitation when not bound to a complementary molecule and a high polarization quantitation when bound.

A method is provided for measuring competitive binding activity of molecules to steroid hormone receptors, comprising: mixing a fluorescence-emitting compound that binds to the steroid hormone receptors in a solution containing the steroid hormone receptors. Measuring the fluorescence polarization of the solution. Then, incubating the solution with at least one molecule that may compete with the compound for interaction with the steroid hormone receptors. Subsequently, measuring the fluorescence polarization of the solution. Finally, comparing the fluorescence polarization measurements to quantify any competitive interaction.

A method is provided for measuring binding activity of molecules to steroid hormone receptors, comprising: mixing a fluorescence-emitting compound that binds to the steroid hormone receptors at a first domain and a fluorescence-labeled nucleic acid that binds to the steroid hormone receptors at a second domain in a solution containing the steroid hormone receptors. Measuring the fluorescence polarization of each fluorescence emission from the solution. Then, incubating the solution with at least one molecule that may compete for interaction with at least one domain. Subsequently, measuring the fluorescence polarization of each fluorescence emission of the solution. Finally, comparing the fluorescence polarization measurements to quantify any interaction.

Also, a kit is provided utilizing the methods listed above for identifying natural and non-natural molecules which bind to human steroid hormone receptors, for use in treating related diseases. The kit comprises instructions for utilizing fluorescence polarization to identify the molecules; a receptacle containing human steroid hormone receptors; and, a receptacle containing fluorescence-emitting hormone which binds human steroid hormone receptors. The kit may further contain a receptacle containing a fluorescence-labeled nucleic acid.

Reference is now made in detail to the preferred embodiments of the invention, examples of which are illustrated in the accompanying drawings.

DETAILED DESCRIPTION OF THE INVENTION

The present invention describes methods by which the association of a fluorescence-emitting compound and a fluorescently labeled oligonucleotide with another macromolecule such as a protein may be measured rapidly, accurately and with high sensitivity in solution. In particular, this invention relates to the detection of complex formation (i.e., formation of a stable, specific noncovalent association) between the compound and/or the oligonucleotide and the target macromolecule, each at very low concentration, through the measurement of the polarization of fluorescence of an intrinsic fluorescence-emitting compound and an extrinsic fluorescent probe covalently coupled to the oligonucleotide. The fluorescence polarization detection is based upon the increase in the rotational correlation time of the fluorophore as a result of the increase in the size of the tumbling particle when the protein or other macromolecule is complexed with it, compared to the rotational correlation time of the fluorophore in the absence of interacting macromolecules. Using the appropriate instrumentation, measurements of fluorescence polarization may be made very rapidly, usually on the order of 5–10 minutes. In contrast, a blot-hybridization or gel retardation analysis may take a full day—and very often longer—to complete. Biological macromolecules are often found in extremely small amounts, requiring analytical sensitivities below nanomolar levels. The method described in the present invention allows measurements to be made at the picomolar level—well within the range required.

It is expected that the method described will be useful in the analysis of proteins, receptor proteins, hormones, oligonucleotides, DNA, RNA and other macromolecules either biological or synthetic. Since the technique described is performed in the solution phase, it is particularly useful in identifying those parameters of the solution which promote or interfere with complex formation between polynucleotides and other macromolecules, for instance, pH, salt concentration, and/or other molecules.

Definitions

A natural human hormone is a chemical substance that is secreted into the body fluids by one cell or a group of cells and that exerts a physiological control effect on other cells of the body. The function of the different hormones is to control the activity levels of target tissues through their interaction with other molecules. A hormone, in general, is herein defined as any substance (natural or synthetic) that may act to exert a physiological response in tissues or bind to molecules normally bound by the natural hormone.

The term "nucleic acid", "polynucleotide", "oligonucleotide" are defined as multiple nucleotides attached in the form of a single or double stranded polynucleotide that can be natural; or derived synthetically, enzymatically, and by cloning methods. The use of the terms RNA and DNA may be used interchangeably in this description and include either double—or single-stranded nucleic acids. However, the preferred embodiments refer to any form of DNA.

A Fluormone is a shortened term for 'fluorescent hormone'. It is any molecule that is covered by the hormone definition and emits fluorescence. Characteristics of a fluormone suitable for use with this method include:

Emission light must be isotropic.

The quantum yield must be sufficiently high over the potential background.

The fluorescent molecule must be biochemically inert.

The fluorescent signal must be stable in an aqueous buffer for a period of time sufficient for the assay to be performed.

The fluorescent hormone must be stable in a plastic 96 or 384 well plate.

The fluormone must have a low polarization value when free and a high polarization when bound.

The fluormone must have a binding affinity tight enough to allow for competition assays.

It must be compatible with solvents used in high throughput screens.

Fluorescence polarization is fully described and defined in U.S. Pat. No. 5,786,139 issued to Burke et al. and incorporated herein by reference. Fluorescence anisotropy can also be used to measure the binding. Like polarization values, it is calculated from the emission intensity in the horizontal and vertical planes. It can be substituted for polarization with a standard mathematical correction.

The method and kit include the use of a light-emitting compound which is used as a label. The present invention utilizes fluorescence polarization techniques to quantify fluorescence light-emitting characteristics. Fluorescence-emitting compounds include any compound having appropriate fluorescence characteristics for use with the invention. One can determine whether or not a particular fluorescence emitting compound is suitable for the present invention by comparing the candidate compound with those compounds illustrated in the Examples. If the candidate compound performs a required function such that a successful detection and quantification can be obtained, similar to the compounds used in this application, the compound is suitable for use with this invention. Potential fluorescence-emitting compounds for use in the invention include, for example, the fluorescence-emitting hormones: THC-ester, THC-ketone, and THC-amide. In the preferred embodiments the THC-ester renamed ES1 for the purposes of this application, is used as the fluormone. Several appropriate estrogen receptor ligands which act as fluormones are described in Hwang et. al. Biochemistry 31:11536–45, 1992, incorporated herein by reference. Other fluorescence-emitting labels useable with this method and the process of their attachment to nucleic acids is fully described and defined in U.S. Pat. No. 5,786,139 issued to Burke et al. and incorporated herein by reference.

Preferred Embodiments

A fluorescence polarization assay is provided for measuring binding of molecules to steroid hormone receptors, and more particularly estrogen receptor, that is independent of fluorescence intensity. A fluorescence-emitting hormone is a small molecule which rotates and tumbles rapidly in solution. Therefore, it has a low polarization value. When the hormone binds to the relatively large receptor protein, its rotation slows significantly and the polarization values rise sharply. The method is homogeneous meaning that it requires no separation step. A fluorescence-emitting hormone and a hormone receptor are mixed in a buffer solution for a sufficient period of time to allow binding and reach equilibrium. Then the polarization value is quantified using an appropriate instrument.

The instrument must be a fluorescence polarimeter device. Standard fluorescence plate readers or spectrometers cannot read polarization values, and instruments retrofitted for polarization are generally less sensitive than dedicated fluorescence polarization instruments. In the preferred embodiments, a single tube Beacon 2000 FP instrument (PanVera Corporation, Madison, Wis.) was used to quantify polarization.

An advantage of fluorescence polarization over fluorescence intensity is the ability to remove unrelated factors from the measurement, such as other molecules which adversely affect intensity. Advantages over other technologies include: 1) FP measurements are performed in solution, allowing molecules to be studied at equilibrium in contrast to other techniques which require the attachment of one of the binding partners to a solid support; 2) FP measurements can be taken every six seconds, making kinetic reactions (associations, dissociations, or enzymatic degradations) easy to follow in real time; 3) FP gives a direct measure of a fluorescence-emitting compound (tracer) bound/free ratio, separation is not required which eliminates filter binding, precipitation, and centrifugation steps; 4) manipulation or alteration of the samples is not required, therefore artifactual loss of signal through handling does not occur; 5) FP measurements do not deleteriously affect the sample—samples can be analyzed, treated, and reanalyzed. 6) FP measurements can be performed at temperatures from 6° C. to 65° C.

In a preferred embodiment, a described method is used to detect molecules that may compete with a Fluormone to a specific receptor domain or interact with another part of the receptor that may affect the Fluormone's receptor binding domain. In another preferred embodiment, a described method allows analysis of how DNA binding to a receptor domain is affected by molecules binding to other receptor domains. The preferred receptor is a steroid hormone receptor and more specifically the human estrogen receptor.

Description of Human Estrogen Receptor

The human estrogen receptor is a 66 kilodalton protein which modulates the actions of estrogens in estrogen responsive tissues. It functions as a transcription factor which binds to estrogen response elements in gene promoters thereby mediating transcription. The protein contains many modular domains, which are conserved among a larger superfamily of nuclear hormone receptors. The estrogen receptor has several domains which are involved in DNA binding, hormone binding, receptor dimerization, transcriptional activation and binding other accessory proteins. All of the domains play critical roles in estrogen receptor function and interplay between the domains is currently a fundamental research inquiry.

The estrogen receptor can function in different capacities in different cell types. It has a significant role in cell differentiation and development, endometrial, liver, breast cancer, and bone mineral density. Millions of women have taken estrogen antagonist Tamoxifen to treat breast cancer. The methods described provide another tool to aid the researcher in efficiently identifying and characterizing unknown proteins and molecules which may interact with estrogen receptor.

Estrogen receptor used in the preferred embodiments is purified and not an extract containing estrogen receptor among other things. Another preferred embodiment utilizes recombinant estrogen receptor obtained from PanVera Corporation, Madison, Wis.

Tetrahydrochrysenes have been described as a class of inherently fluorescent estrogen analogs that bind with high affinity to the human estrogen receptor (ER). One of the compounds called ES1 binds to ER with a dissociation constant of 1 nM, making it an excellent choice as the tracer in a standard competition or displacement reaction. ES1 and ER are incubated together such that approximately 50% of the ES1 is in a bound state, giving ES1 a high polarization value. Compounds added to the ES1/ER complex may compete with ES1 for binding to ER depending on their affinity for ER. The higher the affinity of the competing compound for ER, the lower the concentration of competitor necessary to release ES1 from ER. As the fraction of unbound ES1 increases, the polarization value drops.

Certain nonsteroidal compounds also bind to the ER by way of competition with a natural hormone, estradiol for ER binding domains. Some of these compounds mimic the estrogenic activity of estradiol and have been termed "environmental estrogens." It is a concern that common chemicals such as herbicides and pesticides may enter the body and stimulate estrogen response pathways.

In a preferred embodiment of a competitive assay, a standard curve is developed using a bound fluormone and various concentrations of estradiol. This allows one to determine the amount of estradiol in unknown samples, including tissue samples, foodstuffs, or chemical samples.

In another preferred embodiment, a kit is provided which contains the reagents necessary to perform a competition assay to assess affinity of test compounds for ES. Instructions are provided indicating that ER is added to a solution containing ES1 to form a Fluormone/ER complex with high fluorescence polarization. The complex is then to be added to estrogen competitors in microtiter wells or 6 mm glass tubes. The shift in polarization in the presence of test compounds is used to determine relative affinity of test compounds for ER.

EXAMPLES

Example 1

The polarization of the fluorescent hormone is directly related to the concentration of estrogen receptor and the total shift is polarization is optimal with 535 nm emission.

The optimal excitation and emission wavelengths can change for a give fluorophore depending on which solvent is used. Some choices of wavelengths may give the maximum absorption and emission spectra but they may not give the optimal polarization data. Several combinations of excitation and emission filters were tested to determine which gave the optimal results.

Human recombinant estrogen receptor was serially diluted in ES1 Binding Buffer in 166 mm borosilicate tubes from 200 nM to 12 pM. Fluormone ES1 was diluted in ES1 Binding Buffer and added to each tube so that the concentration was between 1.5 and 1.8 nM in a final volume of 100 $\mu$l. The mixtures were incubated at room temperature for 1 hour in darkness and the polarization values were measured using Beacon 2000 Fluorescence Polarization Instrument. Excitation was done at 360 nm and the emission was measured at either 485 nm (bottom curve) or 535 nm (top curve).

Figure 1:
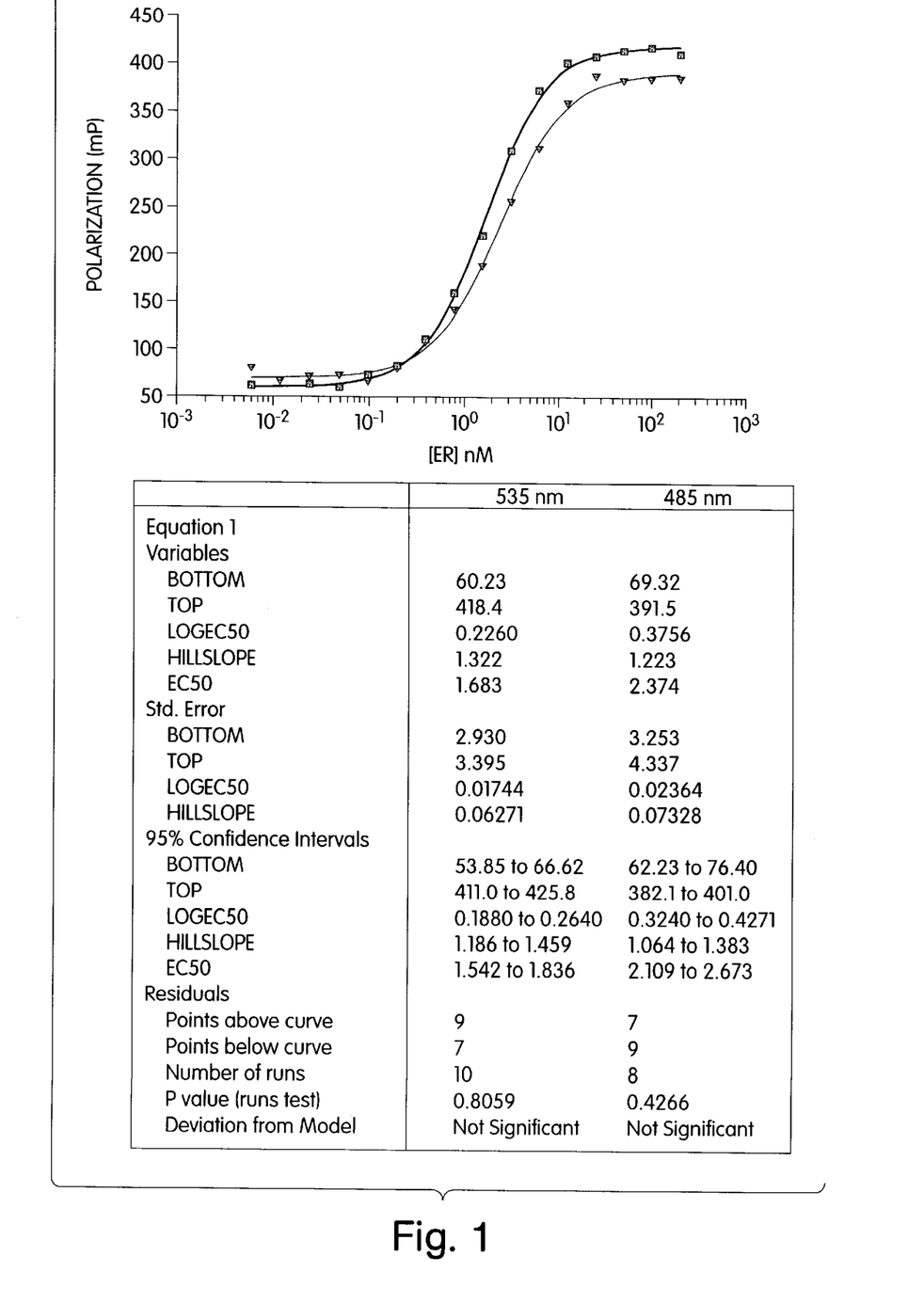
FIG. 1 illustrates that the polarization of the fluorescent hormone is directly related to the concentration of estrogen receptor and the total shift is polarization is optimal with 535 nm emission.

The polarization data were analyzed using Graphpad's Prism program to fit the sigmoidal curve. These data (see FIG. 1) show that the shift in polarization is directly related to the increase in concentration of the estrogen receptor and that the fluormone is saturated at high ER concentrations. It also shows 535 emission filters gives a higher shift in polarization than the 485 mm emission filter with a total polarization shift of 358 mP (418-60). BOTTOM and TOP refer to the minima and maxima of the sigmoidal curve, respectively. All log values are simply the logarithm of that number. The HILLSLOPE is a measure of the cooperativity in the equilibrium binding and the EC50 is the dissociation constant. ES1 Binding Buffer is 40 mM Tris-HCl, pH 7.5, 50 mM KCl, 5% glycerol, 10% dimethylformamide, 0.02% sodium azide, and 50 $\mu$/ml bovine gamma globulin.

Example 2

Fluorescent Estrogen Competition Assay in Single Tube

Figure 2:
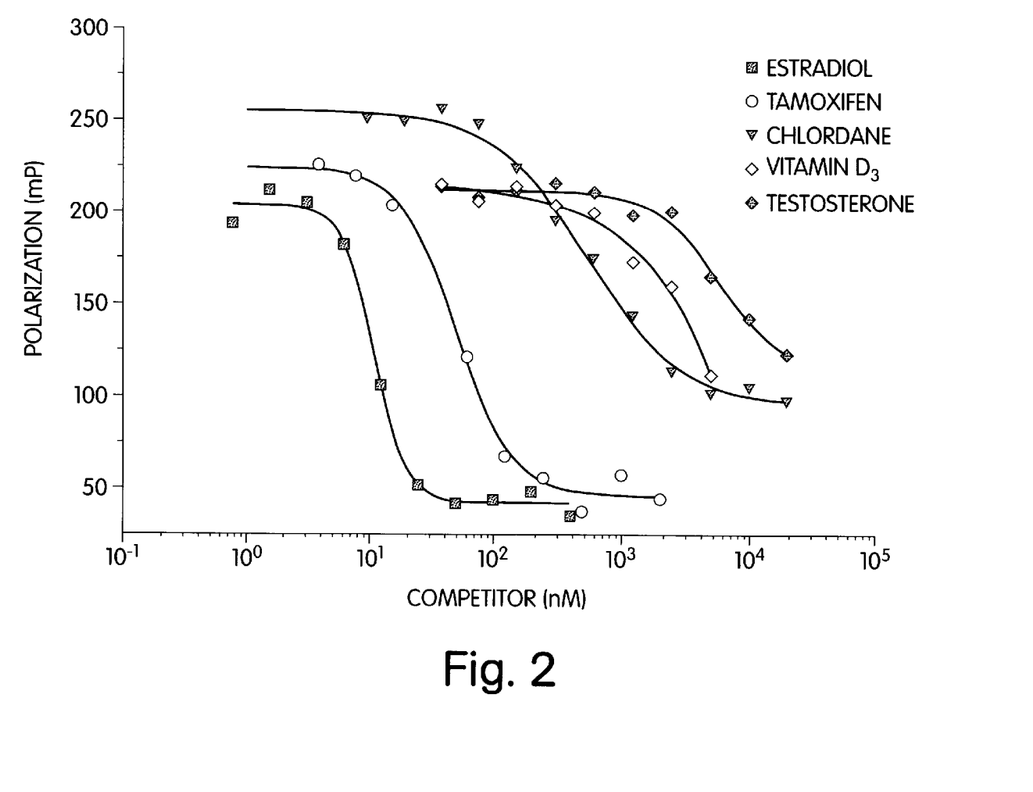
FIG. 2 shows the results of fluorescent estrogen competition assay in single tube.

The assay described in Example 1 can be used to measure the relative binding affinities of other compounds which bind to the estrogen receptor. Conditions were selected such that the fluormone ES1 was bound to the estrogen receptor and compounds were then to compete with binding. If the added compound successfully competed off the fluorescent hormone, then the polarization should drop significantly since the fluormone would go from the bound state to the free state. Several compounds were investigated for their ability to compete with ES1 binding to purified ER. Competitors were serially diluted in ES1 Binding Buffer. Fluormone ES1 and ER were then added to each tube to a final concentration of 1 nM and 5 nM respectively. The three components were allowed to reach equilibrium at room temperature and polarization values were measured using the Beacon 2000 FP instrument. The data were analyzed using a curve fitting program in Graphpad Prism. (see FIG. 2)

Example 3

Fluorescent Estrogen Competition Assay in 96 Well Format

Figure 3:
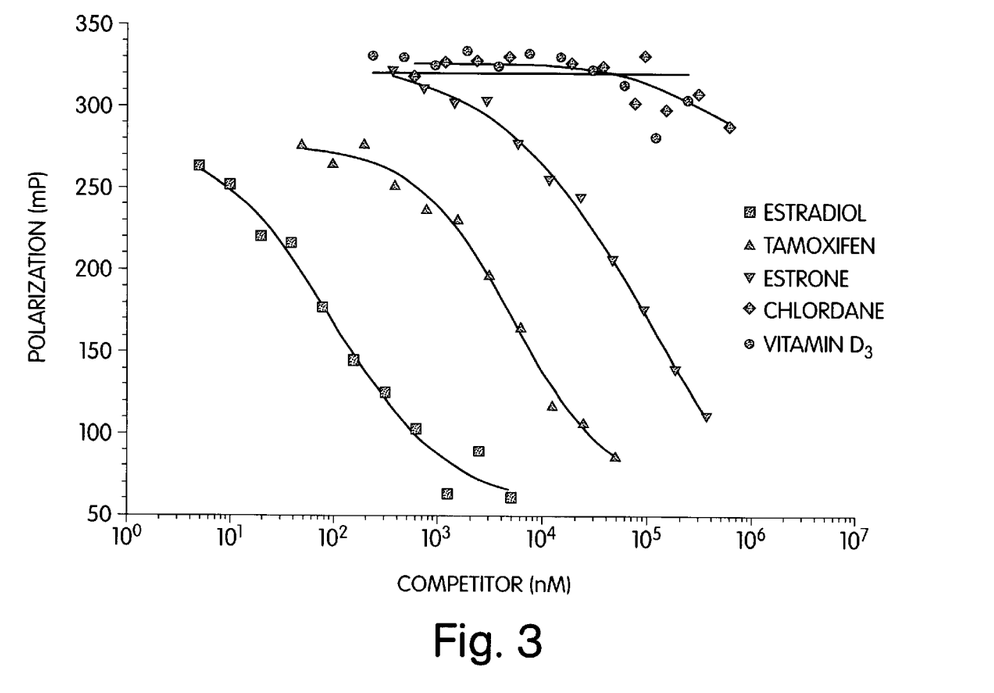
FIG. 3 charts the fluorescent estrogen competition assay in 96 well format.

The experiment was performed as in Example 2 except that the assay required 20 nM ER and 20 nM Fluormone ES1 for the assay and the dilutions were done in 96 well plastic plates. The polarization values were measured (see FIG. 3) using a FPM-2 Fluorescence Polarization Instrument from Jolley Consulting and Research. Test compounds were serially diluted in ES1 binding buffer and added to wells containing the ES1/ER complex. The plates were allowed to equilibrate at room temperature for at least one hour before the polarization values were measured. The total volume in each well was 200 $\mu$l.

Example 4

Specificity of Fluormone binding to ER and BSA.

Figure 4:
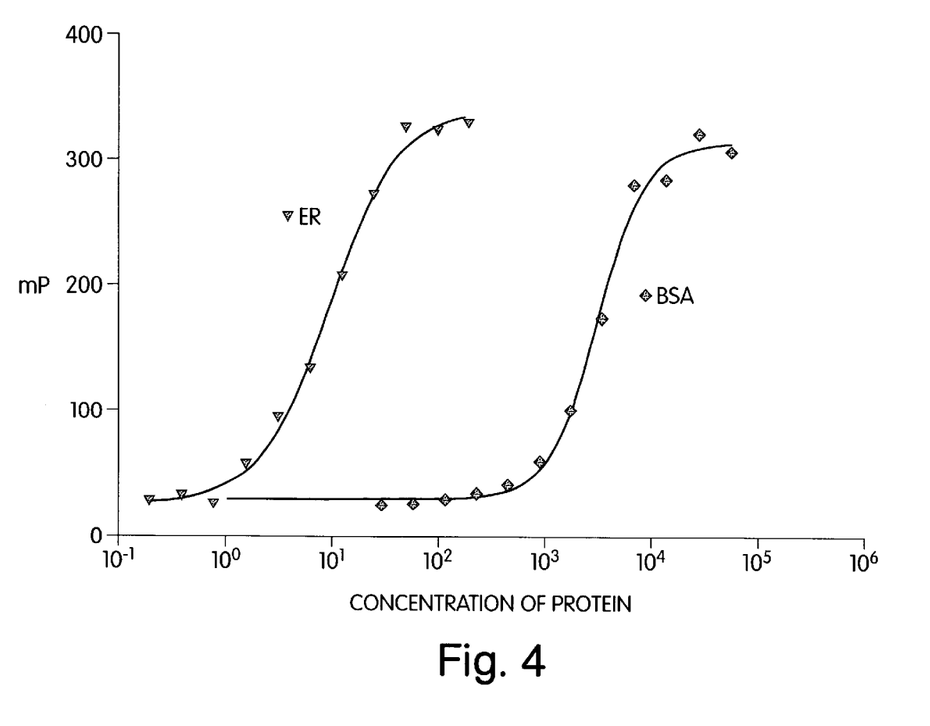
FIG. 4 shows the specificity of fluormone binding to ER and BSA.

Human recombinant estrogen receptor or bovine serum albumin (BSA) were serially diluted in 10 mM Tris-HCl, pH 7.5, 1 mM EDTA. Fluormone ES1 was added to a final concentration of 1 nM. The mixtures were allowed to reach equilibrium for 1 hour at room temperature and the polarization values were measured using a Beacon Fluorescence Polarization Instrument (see FIG. 4). Excitation was at 360 nm and emission was measured at 485 nm. The starting concentration of the ER and BSA were 200 nM and 60 $\mu$M respectively. The concentration of protein is measured in nM and the polarization is measured in mP. This data is significant in that there is over a 500 fold difference in the binding affinities and that even though the binding to BSA is weak, it is very specific and the top of the curve is flat.

Example 5

Figure 5:
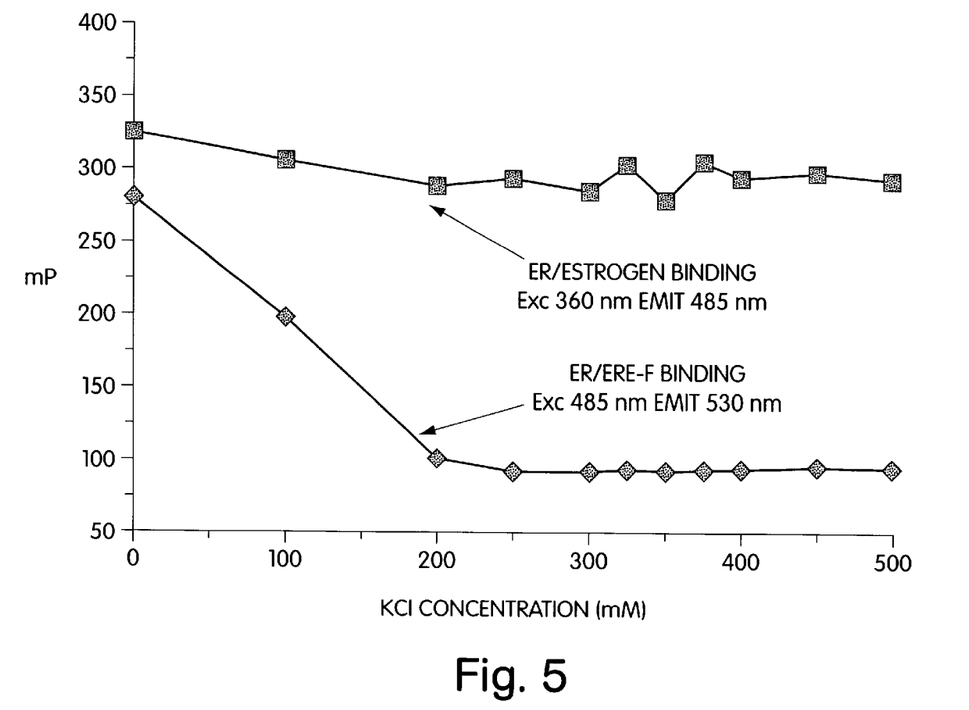
FIG. 5 plots the detection of ER binding to fluormone ES 1 and fluorescein labeled DNA in the same sample.

Detection of ER binding to Fluormone ES1 and Fluorescein labeled DNA in the same Sample One of the fundamental questions in estrogen receptor physiology has been how hormone and DNA binding to estrogen receptor are affected by each other. The present invention allows one to measure binding to both hormone and DNA to the same sample of estrogen receptor. This is possible because the DNA is labeled with fluorescein which has excitation/emission at 485/535 nm and fluormone ES1 has excitation/emission at 360/535 nm. Eleven dilutions (600 μl each tube) of KCl in 10 mM Tris-HCl, pH 7.5 were prepared from 500 mM to 0 mM. Six μl of 100 nM fluormone ES1 and 3 μl 3,000 nM ER were added to each tube. The mixtures were allowed to incubate at room temperature for 1 hour and the polarization values were measured using a Beacon 2000 (see FIG. 5) with 360/535 nm excitation/emission filters. Six μl of 100 nM fluorescein labeled estrogen response element DNA were added to each tube. After equilibrium was reached, the polarization values were measured. The estrogen response element is a 25 basepair double-stranded DNA which is 5' fluorescein labeled. At all KCl concentrations the ES1 bound to the ER but the DNA was bound only at the low KCl concentrations, therefore, the DNA/receptor interaction was shown to be salt dependent over the range studied while the fluormone/receptor interaction was insensitive to salt.

Example 6

Detection of environmental compounds which bind estrogen receptor using a competitive fluorescence polarization assay.

Figure 6:
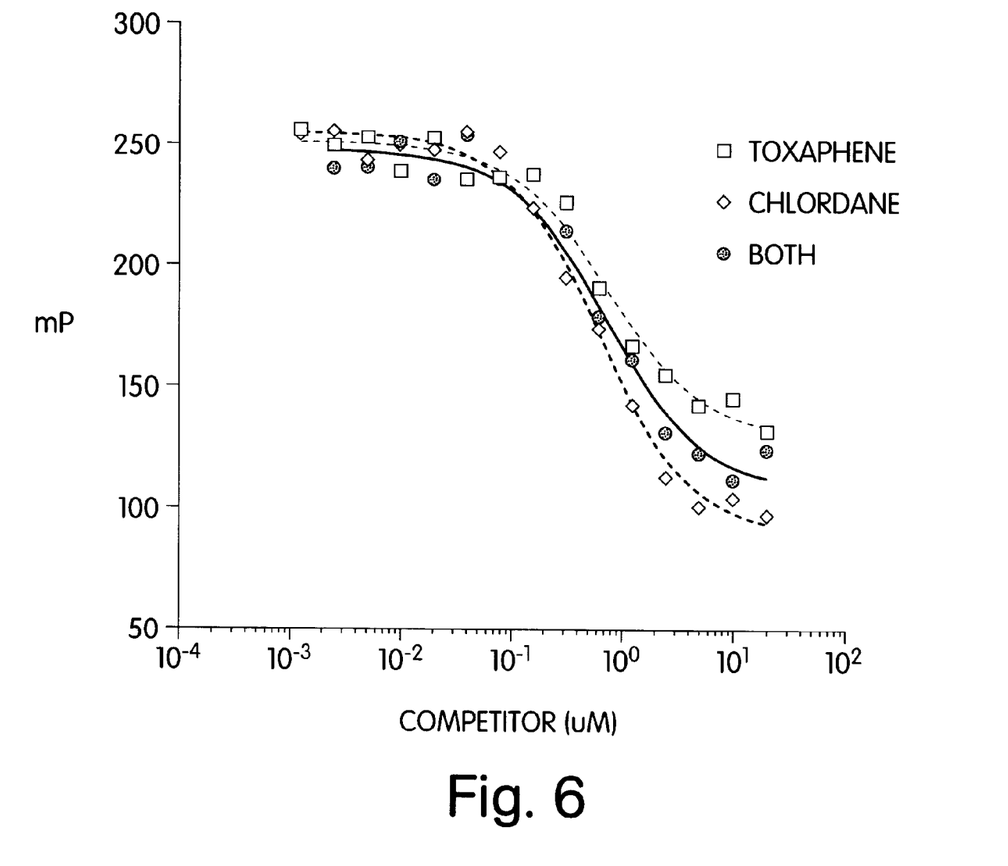
FIG. 6 depicts the detection of environmental compounds which bind estrogen receptor using a competitive fluorescence polarization assay.

Many compounds found in the environment are know to act as natural estrogens. Two pesticides, toxaphene and chlordane, were tested for their ability to displace fluormone ES1 binding to ER. The two pesticides were tested individually and together. The pesticides were diluted in 10 mM Tris-HCl, pH 7.5, 1 mM EDTA, 1 nM fluormone ES1. Estrogen receptor was added to each tube at a final concentration of 10 nM. The mixtures were allowed to equilibrate for 2.5 hours at room temperature and the polarization values were read 360/485 nm excitation/emission. The pesticides effectively competed the fluormone ES1 off the estrogen receptor reducing the polarization value (see FIG. 6) in going form the bound to free state.

Example 7

Figure 7:
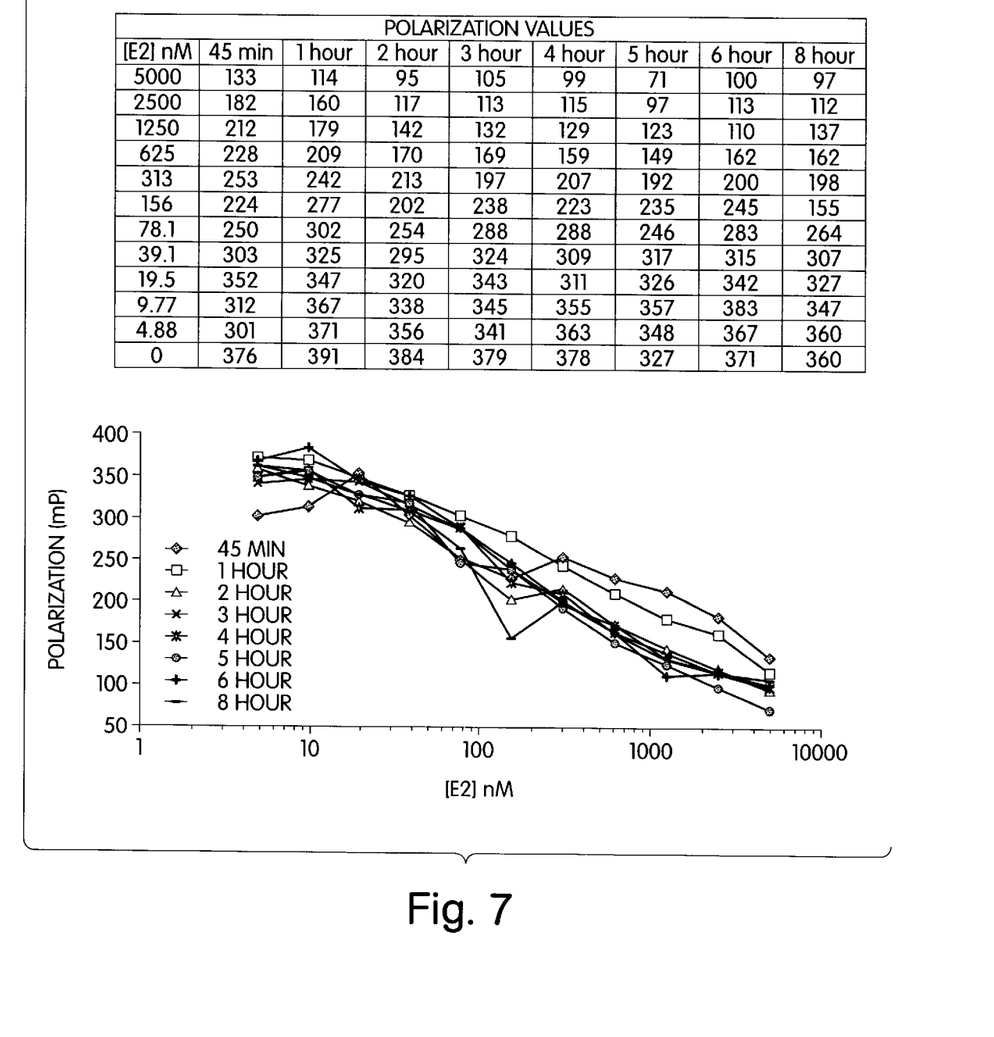
FIG. 7 shows the stability of the ER/fluormone complex in 96 well plastic plates at room temperature.

Stability of the ER/Fluormone Complex in 96 Well Plastic Plates at Room Temperature Typically in a high throughput screen, 100,000 to 1,000,000 compounds are screened for their ability to bind the target molecule. Typically the target is an enzyme or a receptor-like binding partner. The 96 well plates are usually handled in groups of 50 and it is necessary that the assay is stable in the plates for period of time that it takes to 1) fill 50 plates, 2) allow the reaction to go to completion), 3) read the values in all the wells in the 50 plates. We needed an assay that was stable for up to 6 hours at room temperature. To achieve this stability, we tested a large number of compounds for their ability to improve the assay. The estradiol is serially diluted into 11 wells with five replicate rows. As described, the fluormone ES1/estrogen receptor mixture is added to each well and the binding reaction is allowed to reach equilibrium during one hour. The polarization values of the sample in each well is then measured (see FIG. 7). As the amount of estradiol is increased, it completes with the fluormone binding to the ER producing free fluormone which has a low polarization value. At each concentration of estradiol, data was taken at 1, 2, 4, 6, and 8 hours. The assay gives stable data over this time range at room temperature.

Example 8

Determination Of Optimum Fluorescent Hormone For Polarization Assay And DMSO Interference Three fluorescent estrogens were tested in these experiments, THC-ester, THC-ketone, and THC-amide. Fluormone ES1 is the same as the THC-ester and is the fluorescent hormone in the kit. We examined all of these in several different ways: 1) which gave the highest intensity signal at a given concentration, 2) which gave the highest affinity binding to ER yet did not did not show a lot of nonspecific binding to other molecules, 3) which was stable in plastic wells at room temperature over 8 hours in an aqueous buffer, and 4), which showed the least interference in it polarization value with the components in a high throughput assay. Based on the first three criteria, we chose the THC-ester but it had a significant problem in that its polarization was changed by one of the components in the screening assay.

Figure 8:
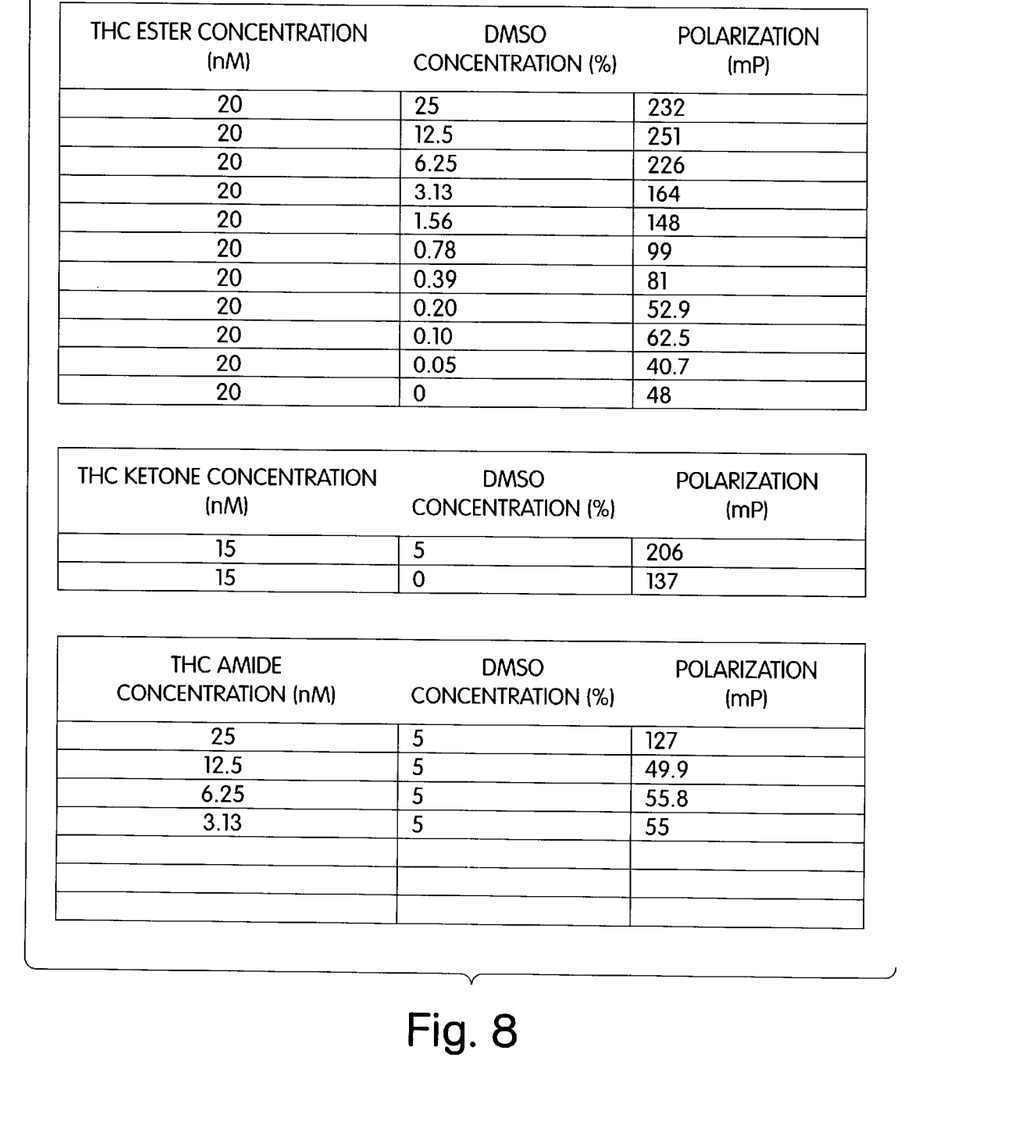
FIG. 8 illustrates the determination of optimum fluorescent hormone for polarization assay and DMSO interference

Compounds that are used in high throughput screens are usually dissolved in DMSO (dimethylsulfoxide). Stocks of compounds are diluted and then added to the reaction so that the final concentration of DMSO is up to 2%. FIG. 8 shows that DMSO affects the polarization of the all three of the fluorescent compounds but to varying degrees. In each case, the fluorescent estrogen, the DMSO, and 10 mM Tris-HCl, pH 7.5 were mixed in a 100 μl volume and the polarization values were measured. The polarization values of the DMSO/fluorescent estrogen were very sensitive to mixing and exposure to glass and plastic. This shift in polarization was also affected by the length of time that fluorescent estrogen was diluted from a high concentration stock in ethanol to a dilute reagent in an aqueous solution. It is for these reasons that the high polarization value caused by the DMSO varies significantly with increasing concentrations. Eliminating the DMSO from the reaction was not an option since many pharmaceutical companies have thousands to millions of compounds dissolved in DMSO.

Example 9

Compounds Investigated to Improve the kit.

Figure 9:
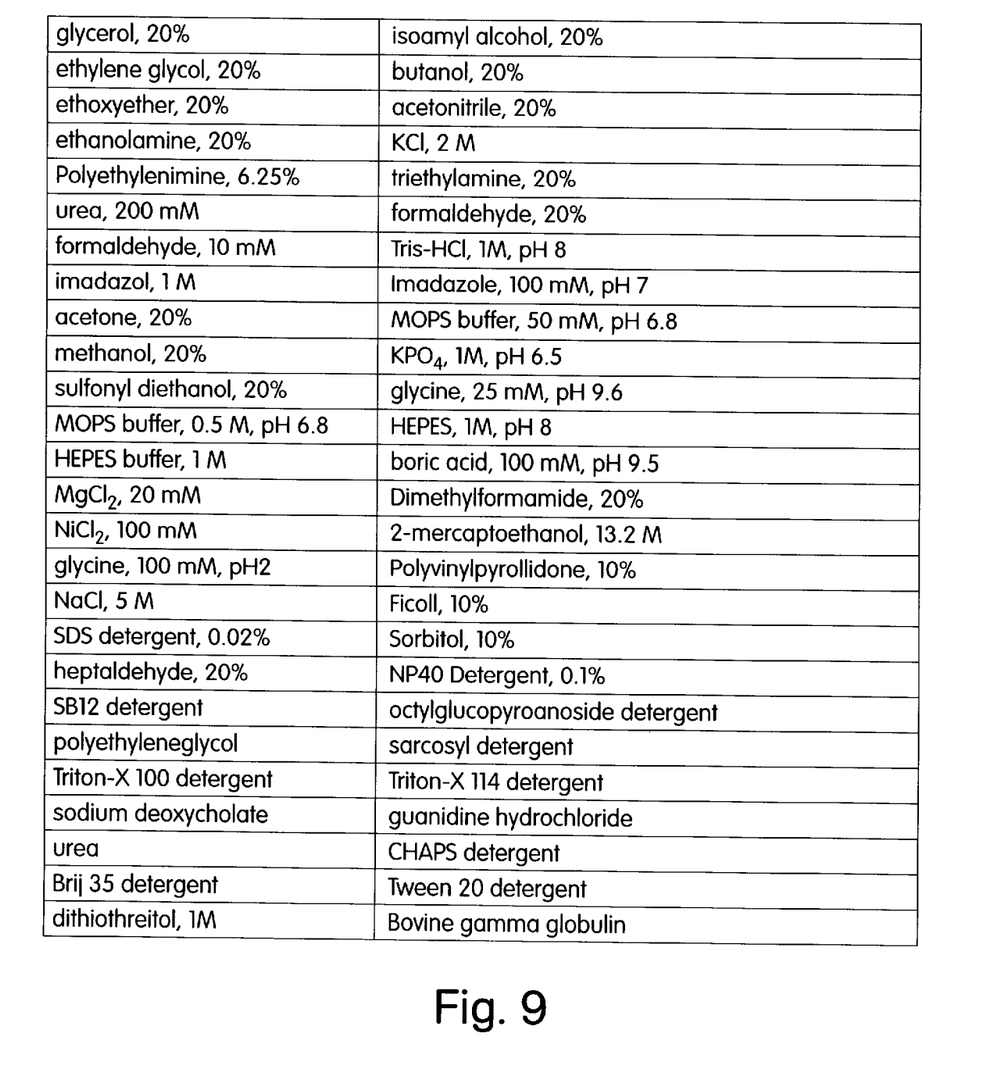
FIG. 9 is a listing of compounds investigated with the method.

We do not understand why DMSO changes the polarization of the fluorescent estrogens but thought that the high polarization might be reduced by other molecules. FIG. 9 lists some of the compounds that we investigated in several ways. We looked at: 1) does the compound affect the polarization and/or intensity of the fluorescent hormone, 2) does it have inherent intensity that interferes with the fluorescent hormone, 3) does it stabilize or destabilize the fluorescent estrogen/ ER complex, and 4) does it stabilize the reaction mixture in 96 well plastic plates at room temperature? Many of the compounds were This list includes several classes of compounds include ionic salts, chaeotropic agents, ionic detergents, non-ionic detergents, organic solvents, proteins, buffers, sugars, and other carbohydrates. Many of these reagents were tested both individually and in combination with other compounds to determine if a class of compounds could be used to improve the assay. Several of the small organic compounds had a corrective effect on the DMSO problem interfering with the fluormone polarization. These compounds were tested further in FIG. 10.

Example 10

Small Organic Molecules Can Correct the Fluormone ES1 Polarization Shift caused by DMSO Several compounds were tested to determine if they could reverse the high polarization shift caused by DMSO. To test the compounds, the following reagents were added to a borosilicate test tube (6 mm OD) at room temperature:
100 μl of 10 mM Tris-HCl, pH 7.5
2 μl 400 nM THC-ester in ethanol
2 μl DMSO
10 μl of one of the compounds in FIG. 10

Figure 10:
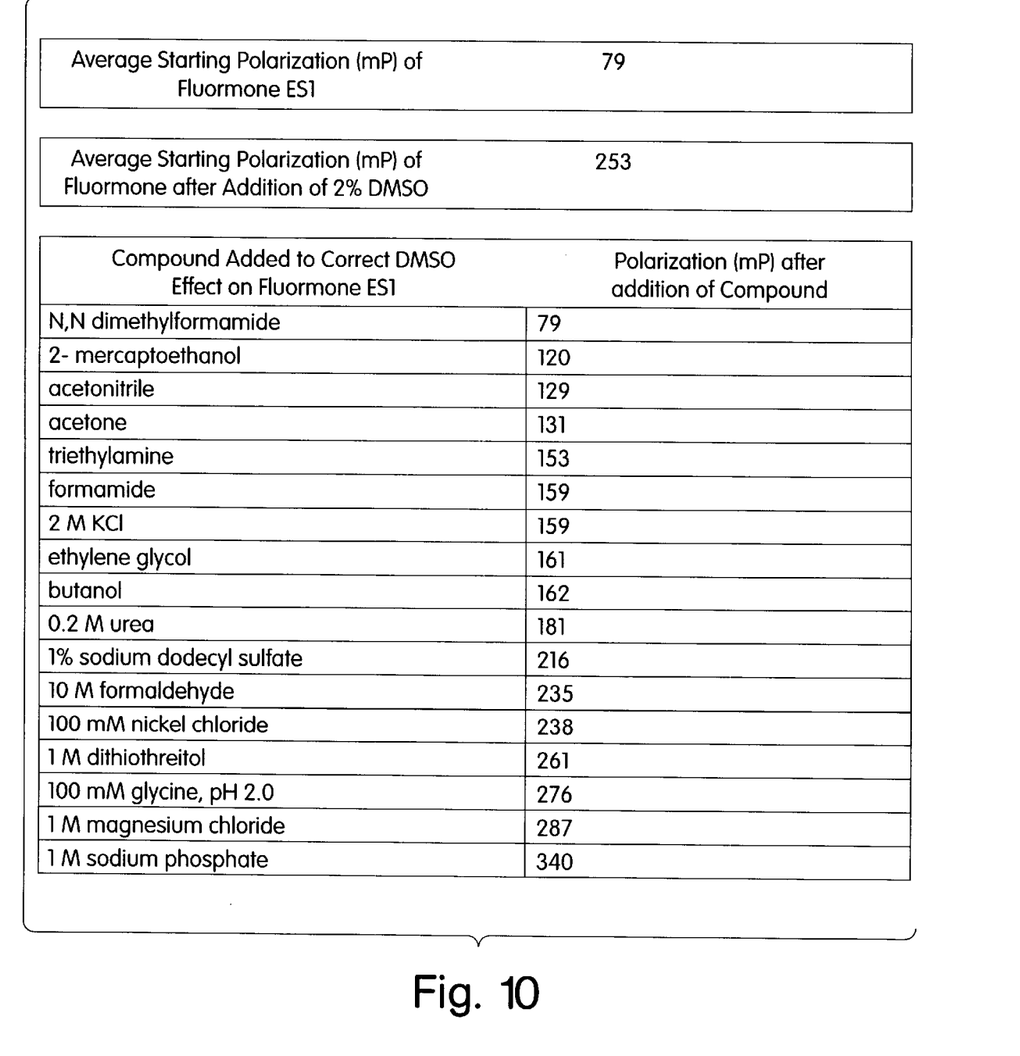
FIG. 10 is a chart listing small organic molecules and polarization values which can correct the fluormone ES1 polarization shift caused by DMSO.

The polarization values were then read using a Beacon 2000 Fluorescence Polarization Instrument. The dimethylformamide gave the best correction of the polarization value and was selected for use in the assay. It is not known why DMSO causes the upward shift in polarization nor why DMF reverses the polarization back down to its normal level. DMF was also tested and shown at concentrations necessary to block the DMSO effects, it did not significantly change fluormone ES1/ER binding.

Example 11

Materials required:

Multiwell fluorescence polarization instrument with suitable 360 nm and 530 nm interference filters or a Beacon© 2000 Analyzer (PanVera Corporation, Madison, Wis.) with 6 mm sample chamber, 360 nm bandpass filter for excitation and a 530 nm interference filter for emission.

Pipetting devices P20, P200, P1000 or suitable repeater pipettors. For pipetting in and out of the 6×50 mm glass tubes, an extra long pipet tip is needed such as the PURE™ XLP tip from Molecular Bio-Products (San Diego, Calif.).

Black, round bottom microtiter plates for use in the multiwell fluorescence polarization instrument (Dynex Technologies, Inc., Chantilly, Va.) or disposable 6×50 mm borosilicate test tubes, certified for use with the Analyzer.

Laboratory timer.

| Description | Composition | Size | Hazard |
|---|---|---|---|
| Estrogen Screening Buffer | 40 mM Tris-HCl, pH 7.5, 50 mM KCl, 5% glycerol, 10% DMF, 50 µg/ml BGG, 0.2% NaN$_3$ | 200 ml | toxic |
| Fluormone ES1 | 4 µM in ethanol | 200 µL | flammable |
| Purified, recombinant, human Estrogen Receptor (ER) | 750 pmoles in 50 mM Tris-HCl, pH 8.0, 50 mM KCl, 10% glycerol, 2 mM DTT, 1 mM EDTA, 1 mM Na VO$_4$ | 750 pmole | irritant |
| dithiothreitol (DTT) | 1M DTT | 1 ml | irritant |

Estrogen Screening Buffer should be stored at room temperature (20–30° C.). Fluormone ES1 at –20° C. and ER at –80° C.

The kit contains enough reagents to perform 384 binding assays using a 100 µL reaction volume. However, the assay may be performed in any size multiwell plate.

| Make 50 µL of 2× complex | | Incubate 1 hour | Read |
|---|---|---|---|
| 1. 38 nM ER | Add 50 µL competitor⇒⇒⇒⇒ | 1. 19 nM ER | Fluorescence |
| 2. 40 nM Fluormone ES1 | | 2. 20 nM Fluormone ES1 | Polarization |
| 3. 10 mM DTT | | 3. 5 mM DTT | Value |
| | | 4. Competitor | |

A competition curve will be generated by adding an aliquot of the 2× Fluormone ES1/ER complex to a serial dilution series of the test compound. The polarization will be plotted against test compound concentration. The concentration of the compound that results in a half maximum shift equals the IC$_{50}$ (concentration of competitor needed to displace 50% of Fluormone) of the test compound Using the table below, make enough of the 2× complex for all of the reactions required. A volume of 50µL of 2× complex is needed for each reaction tube. The concentration of this 2× solution is 40 nM Fluormone ES1, 38 nM ER, and 10 mM DTT in Estrogen Screening Buffer. The Fluormone ES1 is dissolved in ethanol and is therefore quite volatile. Keeping this reagent on ice will not only aid in its stability, but reduce its volatility. 0.5 µL of the Fluormone ES1 and DTT is needed for each reaction. The ER concentration is variable, therefore the amount to add to make the 2× complex must be calculated using the following formula. Write in the number of reactions needed [A], the concentration of the ER (taken from the Certificate of Analysis) [B] and calculate the volume of ER in µL needed [C].

\# of reactions as needed [A]_____×1.9 pmoles/reaction ÷[ER] in pmole/µL [B]

_____=µL of ER needed [C]_____.

The table below is a recipe for making the complex assuming the ER concentration is 1.2 pmole/µL.

| Number of tubes [A] | 4 µM Fluormone ES1 | ER [C] | 1M DTT | Screening Buffer | Final Volume (50 µL/reaction) |
|---|---|---|---|---|---|
| 50 | 25 µL | 79 µL | 25 µL | 2.37 ml | 2.5 ml |
| 250 | 125 µL | 396 µL | 125 µL | 11.85 ml | 12.5 ml |

Serially dilute the test compound in Estrogen Screening Buffer. If there is any information as to the approximate equilibrium constant of the test compound, make certain the dilution series covers test compound concentrations from 100 fold greater to 25 fold less than the Kd.

Add 50 µL of each test compound concentration to 6×50 mm Beacon® tubes. Include 1 tube with 50 µL of Estrogen Screening Buffer for a "no test compound" control. Add 50 µL of 2× complex to each tube, mix well, and incubate all tubes at room temperature for 1 hour.

Measure Polarization Values

The polarization data should be plotted against the Log of the test compound concentration. The concentration of the test compound that results in a 50% shift in polarization is the IC$_{50}$, and is a measure of the relative affinity of the test compound for ER.

The foregoing is considered as illustrative only of the principles of the invention. Further, since numerous modifications and changes will readily occur to those skilled in the art, it is not desired to limit the invention to the exact construction and operation shown and described. Therefore, all suitable modifications and equivalents fall within the scope of the invention.

We claim:

1. A method for measuring the ability of a compound to affect the binding of molecules to a steroid hormone receptor, comprising:

a. providing a solution comprising a fluorescence-emitting compound that binds to the steroid hormone receptor at a first domain; a fluorescence-labeled nucleic acid that binds to the steroid hormone receptor at a second domain; and the steroid hormone receptor;

b. measuring the fluorescence polarization of said fluorescence-emitting compound and said fluorescence-labeled nucleic acid present in the solution from step a) at excitation and emission wavelengths corresponding to the excitation and emission wavelengths of each of said fluorescence-emitting compound and said fluorescence-labeled nucleic acid;

c. incubating the solution of step a) with at least one unlabeled compound that may affect the binding of said fluorescence-emitting compound or said fluorescence-labeled nucleic acid to said steroid hormone receptor;

d. measuring the fluorescence polarization of said fluorescence-emitting compound and said fluorescence-labeled nucleic acid present in the solution from step c) at excitation and emission wavelengths corresponding to the excitation and emission wavelengths of each of said fluorescence-emitting compound and said fluorescence-labeled nucleic acid; and, e. comparing the fluorescence polarization measurements of step b) with step d) to determine if said unlabeled compound affects the binding of said fluorescence-emitting compound or said fluorescence-labeled nucleic acid to the steroid hormone receptor.

2. The method of claim 1 wherein the steroid hormone receptor is purified.

3. The method of claim 2 wherein the purified steroid hormone is a recombinant steroid hormone receptor.

4. The method of claim 2 wherein the difference in fluorescence polarization between the bound and unbound fluorescence-emitting compound and between the bound and unbound fluorescence-labeled nucleic acid is of sufficient magnitude to be suitable for use with a screening assay.

5. The method of claim 4 wherein the screening assay is performed on a multi-well plate.

6. The method of claim 2 wherein the fluorescence-emitting compound comprises a hormone that inherently emits fluorescence.

7. The method of claim 3 wherein the steroid hormone receptor comprises an estrogen receptor.

8. The method of claim 2 wherein the nucleic acid comprises a deoxyribonucleic acid.

9. The method of claim 8, wherein said nucleic acid is a double-stranded DNA molecule.

* * * * *